[19] United States Patent
Ichikawa et al.

[11] Patent Number: 4,799,018
[45] Date of Patent: Jan. 17, 1989

[54] AIR FUEL RATIO MEASURING SYSTEM

[75] Inventors: Norio Ichikawa, Mito; Takayuki Itsuji; Masayuki Miki, both of Katsuta, all of Japan

[73] Assignees: Hitachi, Ltd., Tokyo; Hitachi Automotive Engineering Co., Ltd., Katsuta, both of Japan

[21] Appl. No.: 84,077

[22] Filed: Aug. 11, 1987

[30] Foreign Application Priority Data

Aug. 27, 1986 [JP] Japan .................. 61-198890

[51] Int. Cl.$^4$ .............. G01N 27/62; G01N 27/66
[52] U.S. Cl. .................. 324/465; 324/464; 204/406
[58] Field of Search .......... 204/15, 406, 425; 324/464, 465, 71.5

[56] References Cited

U.S. PATENT DOCUMENTS

| 4,578,171 | 3/1986 | Yamada et al. | 204/406 |
| 4,626,338 | 12/1986 | Kondo et al. | 204/15 |
| 4,664,773 | 3/1987 | Suzuki et al. | 204/406 |

FOREIGN PATENT DOCUMENTS

| 179351 | 10/1983 | Japan . |
| 155853 | 7/1986 | Japan . |
| 180131 | 8/1986 | Japan . |

Primary Examiner—Reinhard J. Eisenzopf
Assistant Examiner—Anthony L. Miele
Attorney, Agent, or Firm—Fay, Sharpe, Beall, Fagan, Minnich & McKee

[57] ABSTRACT

A detecting element (6) comprising a solid zirconia electrolyte (6a), a reference electrode (6d), a detecting electrode (6c) and a diffusion member (6a) is provided, and also a driving circuit (1b, 4) for impressing a voltage between the electrodes (6c, 6d) of said detecting element so as to detect the threshold current of an oxygen ion pumping current ($I_p$) is provided. The output of this driving circuit is delivered as a continuous output ($V_o$) of an air fuel ratio of fuel gas comprising al the regions of rich, stoichiometric and lean air fuel ratios. On the other hand, an $I_p$ detection resistor (Rs) for detecting the pumping current flowing between the input/output terminals of the driving circuit is provided. The opposite-end voltages ($V_a$, $V_o$) of this $I_p$ detection resistor are compared by a comparator (5), and a step signal corresponding to the stiochiometric air fuel ratio ($\lambda$) is outputted from this comparator.

10 Claims, 2 Drawing Sheets

AIR FUEL RATIO MEASURING SYSTEM

FIELD OF THE INVENTION

The present invention relates to an air fuel ratio measuring system, and particularly to an air fuel ratio measuring system suitable for detecting an air fuel ratio from the components of combustion gas of automobiles.

BACKGROUND OF THE INVENTION

In a conventional system for detecting lean and stoichiometric air fuel ratios without switching of circuits, in general, a specified voltage lower than an electromotive force shown on the rich air fuel ratio operation and higher than an impression voltage generating a threshold current value whereat a pump current takes a certain value, is impressed between two electrodes of a detecting element, the lean air fuel ratio is detected thereby as a continuous output from 0 to plus, a rich air fuel ratio is detected as a negative voltage corresponding to the difference between the electromotive force generated in a sensor and the aforesaid impression voltage, which is corresponding to a pump current in an inverse direction against the pump current in a lean air fuel ratio operation, and the stoichiometric air fuel ratio is detected by an output which changes sharply from 0 to minus, as is described, for instance, in FIGS. 4 and 7 of Japanese Patent Laid-Open No. 179351/1983 entitled "Oxygen Density Detecting Method", which was laid open in Japan on Oct. 20, 1983.

Since a signal of a rich region containing the stoichiometric air fuel ratio ( $\lambda=1$ ) is a negative output, as shown in FIGS. 5 and 6 of the above-described prior art, the rich region needs to be inverted into a positive signal to be processed by a computer. Moreover, two different output values are present in $\lambda=1$, in the course from the rich side to $\lambda=1$, and in the course from the lean side to $\lambda=1$, since a signal on the rich side and a signal on the lean side change sharply at a stoichiometric air fuel ratio point. Accordingly, this causes a drawback that the processing of the signal of $\lambda=1$ is complicated. Furthermore, when the negative output on the side of rich is inverted to a positive output to obtain two positive outputs, whether the aforesaid output is the one on the rich side must be determined.

The above-stated problem is settled by a sensor processing circuit in which a potential ground $V_{PG}$ from 0 to a positive value is added to a reference potential of an $O_2$ sensor over all the regions from the rich to the lean to obtain a continuous positive output voltage, as shown in FIG. 1 of Japanese Patent Laid-Open No. 180131/1986 entitled "Tri-state Air Fuel Ratio Sensor for Automobile", which was laid open in Japan on Aug. 12, 1986, for instance.

However, even this publicly-known example of Japanese Patent Laid-Open No. 180131/1986 can not get rid of a fault which makes it impossible to obtain a step signal at the point ($\lambda=1$) of the stoichiometric air fuel ratio, as is the case with the present $O_2$ sensor, while obtaining the extensive continuous output of the air fuel ratio.

SUMMARY OF THE PRESENT INVENTION

An object of the present invention is to obtain an extensive continuous output of an, air fuel ratio, a function of outputting a step signal showing only a stoichiometric air fuel ratio point, and a control signal of $\lambda=1$ whereby the catalytic purification efficiency for purifying CO, $NO_x$ and HC in an exhaust gas can take the best value.

The above-stated object is attained by utilizing the knowledge that the direction of a pumping current caused by oxygen ions is shifted in accordance with the change of an air fuel ratio from the rich to the lean and from the lean to the rich, and by comparing the opposite-end voltages of a resistor, which is a pump current detecting means, for instance, by means of a comparator having a function of differential amplification.

The step signal, which is equivalent to that of the existing $O_2$ sensor of the electromotive force type, can be obtained by setting the continuous output as an input to a comparator so that the comparator output is low in the lean region, i.e. in the case when the pump current is positive, and that it is high in the rich region, i.e. in the case when the pump current is negative, as will be made apparent by a subsequent description.

According to the present invention, a signal output equivalent to $\lambda=1$ can be obtained while the rich to lean air fuel ratio is measured as a continuous output.

DETAILED DESCRIPTION OF THE PREFERRED EMBODIMENT

Figure 1:
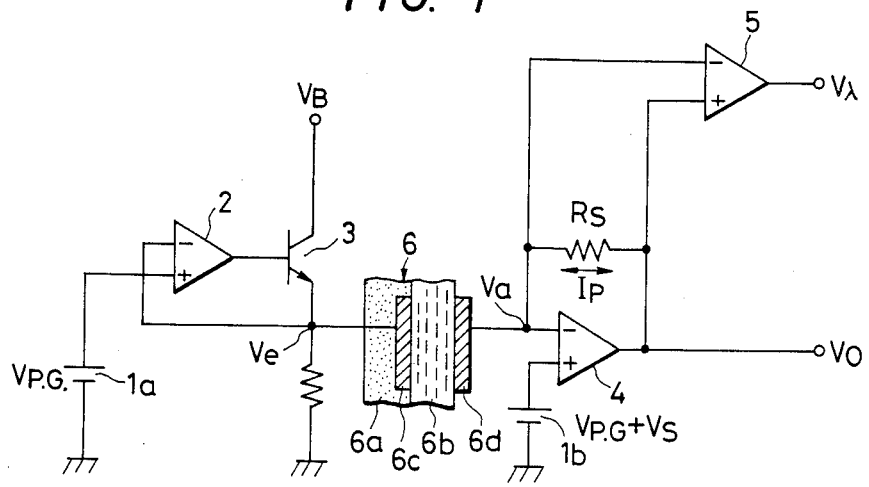
FIG. 1 is a circuit diagram showing a construction of a sensor driving circuit, which is one embodiment of the present invention.
Figure 2:
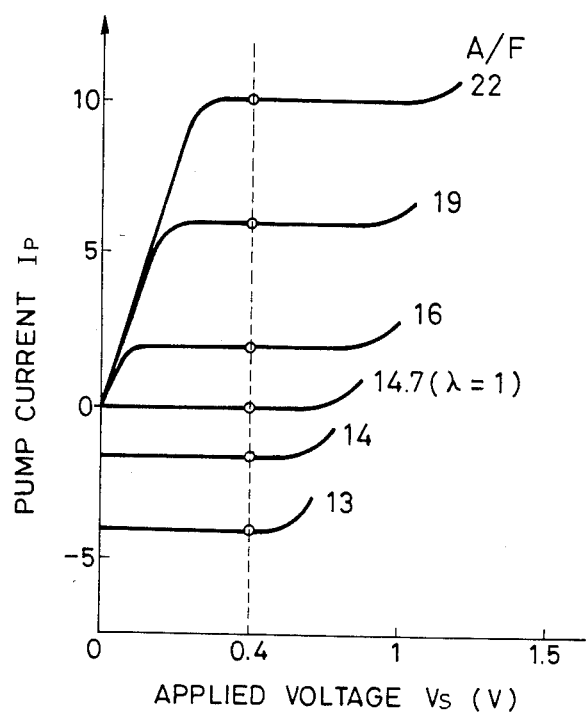
FIG. 2 is a V-I characteristic diagram showing the relationship between a pump current of a detecting element and a sensor interpole voltage.
Figure 3:
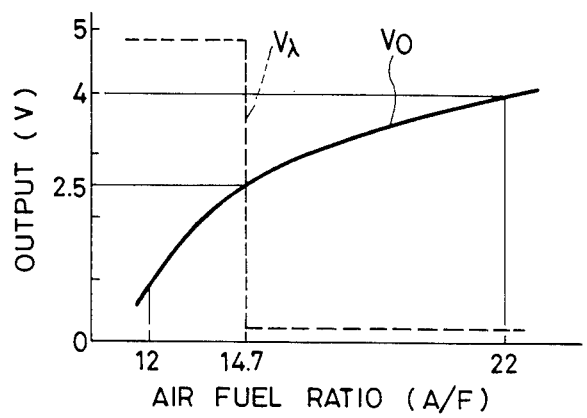
FIG. 3 is a characteristic diagram showing an output characteristic of the sensor driving circuit of the present invention.

FIG. 1 shows a part of the closed tubular detector 6 which part may be conventional and as shown in FIG. 3 of U.S. Pat. No. 4,664,773 issued May 12, 1987. A detecting electrode 6c on the exhaust gas side and a reference electrode 6d, on the atmosphere gas side each of which is formed by platinum electroless plating or the like, are respectively provided on the opposite sides of a solid zirconia electrolyte 6b, which is a solid oxygen ion conductor. A diffusion resistance layer 6a regulating the velocity of diffusion of gas is provided around the detecting electrode. The voltage $V_e$ of the detecting electrode 6c is fed back negatively to an amplifier 2. The current flowing through transistor 3 is controlled by the amplifier 2 so that the voltage Ve can be controlled to be equal to a reference voltage $V_{P.G.}$ even when a pump current $I_p$ flowing through the detecting element 6 is varied. On the other hand, the voltage $V_a$ of the reference electrode $6d$ is controlled to be equal to $V_{P.G.}+V_s$, where Vs is an applied voltage. The current making oxygen ions flow between the detecting electrode $6c$ and the reference electrode $6d$ in the detecting element 6, i.e. the pump current $I_p$, is controlled by a driving circuit of an air fuel ratio measuring system of the present application. Thereby the potential difference between the electrodes $6c$ and $6d$, that is the interpole voltage of the detecting element is adjusted toward the applied voltage $V_s$. The reference voltage $V_{P.G.}$ is generated by first reference voltage generating source $1a$. The added reference voltage equal to $V_{P.G.}$ and the applied voltage $V_s$ are generated by a second reference voltage generating source $1b$. The applied voltage $V_s$ is set herein at a value providing a range of values of the pump current $I_p$ as threshold current, e.g. 0.4 V, in the V-I characteristic illustrated in FIG. 2.

When an air fuel ratio is lean, the interpole voltage of the detecting element 6 turns lower than $V_s$, and therefore oxygen ions flow from the detecting electrode $6c$ toward the reference electrode $6d$ so as to make the interpole voltage, Va−Ve, approach the applied voltage $V_s=0.4$ V. In other words, the pump current $I_p$ is made to flow from the reference electrode $6d$ toward the detecting electrode $6c$ by the amplifier 4.

When the air fuel ratio is of the flow when the air fuel ratio is rich, the interpole voltage turns, in this case, to be higher than $V_s$, and therefore the oxygen ions move in the reverse direction to that lean. In other words, the pump current $I_p$ is made to flow from the detecting electrode $6c$ toward the reference electrode $6d$ by the amplifier 2.

A wide-range continuous output $V_o$ representing the air fuel ratio can be determined by the following equation, based on the pump current flowing through an $I_p$ detection resistance Rs.

$$V_o = V_a + I_p \cdot Rs \quad (1)$$
$$= (V_{P.G.} + V_s) + I_p \cdot Rs$$

Since $V_{P.G.}$, $V_s$ and Rs are constants in this expression, $V_o$ is varied subordinately only by $I_p$. The pump current $I_p$ takes a certain value in accordance with the air fuel ratio (excess air rate λ) due to the V-I characteristic of the detecting element 6 shown in FIG. 2, and therefore the air fuel ratio can be measured by detecting the pump current $I_p$. As is apparent also from FIG. 2, $I_p=0$ at the stoichiometric air fuel ratio (A/F=14.7), and $I_p>0$ in the lean region, while $I_p<0$ in the rich region. Given that $V_{P.G.}=2.1$ V and $V_s=0.4$ V in the equation (1), the air fuel ratio can be measured as a linear output which is $V_o=2.5$ V on the occasion of $I_p=0$, i.e. at the stoichiometric air fuel ratio, as shown in FIG. 3. By using this continuous voltage output, an arbitrary control of the air fuel ratio can be conducted.

Now, a description will be made on a method for obtaining a stepshaped ON-OFF signal equivalent to the one of the prior art O$_2$ sensor of the electromotive force type shown in U.S. Pat. No. 4,212,720 issued July 15, 1980, for the purpose of a ternary feedback control (stoichiometric air fuel ratio point control) which enables the attainment of the best purification efficiency of a catalyzer.

As is described previously, the sign of the value of the pump current $I_p$ varies about a zero point corresponding to the stoichiometric air fuel ratio as a boundary. In other words, the direction of the flow of $I_p$ shown in FIG. 1 is shifted thereat as shown in FIG. 2. Accordingly, a means to detect this state or sign of shifting of the direction of the pump current and a means to deliver said state as a step signal output are provided so as to obtain an output distinctively from the aforesaid continuous wide range output $V_o$. In FIG. 1, concretely, the comparison by a comparator 5 between the opposite-end voltages $V_a$ and $V_o$ of an $I_p$ detection resistor detecting a pump current value is adopted as a means to detect the shifting in the direction of the pump current $I_p$, and a circuit construction is adopted in which a differential amplifier is used as said comparator to obtain a step signal. Since the pump current $I_p$ flows from the detecting electrode $6c$ toward the reference electrode $6d$ in the rich region, $V_o<V_a$ according to this simple circuit construction, and if the comparator 5 comparing the opposite-end voltages of the $I_p$ detection resistor is connected so that the plus input voltage thereof be $V_o$ and the minus input voltage thereof $V_a$, a λ=1 signal output, i.e. Vλ, delivered from the comparator 5 having a function of differential amplification becomes a high output in the rich region, as shown in FIG. 3. In contrast with this, $V_o>V_a$ in the lean region, and said signal output becomes a low output.

By the above-described circuit construction, the λ=1 signal output Vλ varying in a stepped manner at the stoichiometric air fuel ratio (λ=1) can be obtained distinctively and separately from the wide range linear output $V_o$.

Figure 4:
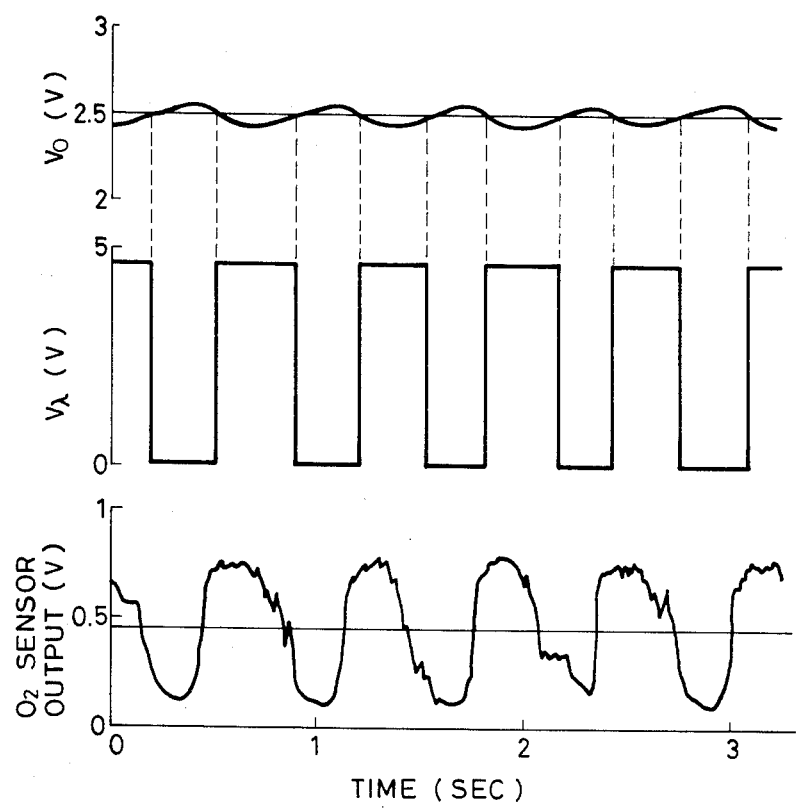
FIG. 4 shows experimental data obtained by comparing simultaneously the characteristics of outputs on the occasion of stoichiometric air fuel ratio control in an actual engine.

FIG. 4 shows one example (the characteristic obtained when Road/Load, R/L, is set to correspond to 60 km/h) of the results of an experiment wherein the ternary feedback control (λ=1 control) was conducted by using the conventional electromotive force type O$_2$ sensor in an actual engine of 2.0 l and four cycles. In the experiment, the signal output of Vλ, as well as variations in the wide range output $V_o$ and the electromotive force of the O$_2$ sensor, were recorded by a wave memorizer. These outputs represent variations in the air fuel ratio observed when an air fuel ratio control is conducted by the O$_2$ sensor.

The wide range output $V_o$ is adjusted so that it is 2.5 V at the stoichiometric air fuel ratio point of A/F=14.7 (λ=1), as shown in FIG. 3. Above and below $V_o=2.5$ V, the λ=1 signal output Vλ repeats electrically to be a high output ($I_p<0$, in the rich region) and a low output ($I_p>0$, in the lean region), corresponding to the shift of the direction of the pump current $I_p$. The cycle of the repetition is 600 to 700 msec. The variation of the output of the O$_2$ sensor is synchronous with the variation of Vλ, and it was also confirmed that the cycle thereof was equal to 600 to 700 msec.

Moreover, the value of Vλ reduced to 1/5 was substituted for the ON-OFF signal of the O$_2$ sensor and the ternary feedback was conducted with respect to the aforesaid engine. Thereby the results equivalent to those shown in FIG. 4 were obtained, in which 10-mode fuel cost was 10.5 km/l, while 10-mode exhaust values were 0.82 g/km of CO, 0.14 g/km of HC 0.19 g/km of $NO_x$. Thus, the results equivalent to those of the control by the $O_2$ sensor could be obtained.

According to the present invention, a signal output being equivalent to $\lambda=1$ and independent of a wide range continuous output can be obtained only by providing a simple circuit construction additionally.

Moreover, a signal equivalent to the one of the existing $O_2$ sensor of the electromotive force type can be obtained as another effect, and it can be used well as a signal used exclusively for ternary feedback control for bringing an air fuel ratio to the stoichiometric air fuel ratio point at which the catalyzer purification efficiency is the maximum.

What we claim is:

1. In an air fuel ratio measuring system that measures the air fuel ratio of fuel gas burned to produce an exhaust gas and that provides an output signal Vo that varies continuously corresponding to the air fuel ratio over all of the rich, stoichiometric and lean air fuel ratios, said system having a detecting element having a solid oxygen ion electrolyte, a reference electrode and a detecting electrode on the opposite sides of the electrolyte, respectively, a diffusion layer controlling a quantity of oxygen molecules arriving at the detecting electrode, and driving circuit means for impressing an interpole voltage between said electrodes so as to pump oxygen ions in one of two directions to detect a pump current between the electrodes, wherein the improvement is in said driving circuit comprising:

first source means generating a constant potential ground reference voltage $V_{P.G.}$;

first control means connected to said detecting electrode for controlling the voltage of said detecting electrode to approach $V_{P.G.}$, when the pump current is varied;

second source means generating a constant second reference voltage equal to the sum of said $V_{P.G.}$ and an applied voltage $V_s$;

second control means connected to said reference electrode for controlling the voltage of said reference electrode to approach said second reference voltage $(V_{P.G.}+V_s)$ so that the interpole voltage between the electrodes of said detecting element is controlled to said applied voltage $V_s$, and said second control means generating the output signal Vo that varies continouusly and is correlated to the air fuel ratio changes throughout lean stoichiometric and rich air fuel ratios;

first detecting means connected between said reference electrode and the output signal of said second control means for detecting the pump current corresponding to the air fuel ratio and outputting a continuous detecting signal that varies continuously and changes in sign from rich to lean air fuel ratios at the stoichiometric value; and second detecting means connected to said first detecting means to receive said detecting signal for detecting the sign change of the pump current and outputting a step signal $V\lambda$ that changes in correlation to a change in pump current sign, whereby said continuous output signal $V_O$ is delivered from said second control means and the step signal is delivered from the second detecting means over the full range of lean, stoichiometric and rich air fuel ratios.

2. The air fuel ratio measuring system according to claim 1, including a source voltage, and wherein said first control means comprises an amplifier having a non-inverting input terminal connected to said reference voltage $V_{P.G.}$, transistor connected between said source voltage of the detecting electrode, impedance menas connected from said detecting electrode to ground, means feeding the voltage of said detecting electrode back to an inverting input terminal of said amplifier, and the output of said amplifier being connected to the control terminal of said transistor.

3. An air fuel ratio measuring th system according to claim 1, wherein said second control means comprises an amplifier having an inverting input terminal connected to said reference electrode, a non-inverting input terminal of the amplifier being connected to ground through said second source means for receiving the second reference voltage, the output of said amplifier providing said continuous output signal Vo, and said first detecting means being connected between the inverting terminal of said amplifier and the output terminal of said amplifier.

4. The air fuel ratio measuring system according to claim 3, wherein said first detecting means comprises a resistor.

5. The air fuel ratio measuring system according to claim 4, wherein said second detecting means comprises a differential amplifier having its input terminals connected to opposite ends, respectively, of said resistor.

6. The air fuel ratio measuring system according to claim 3, wherein said second detecting means comprises a differential amplifier having input terminals respectively connected across said first detecting means.

7. The air fuel ratio measuring system according to claim 2, wherein said second control means comprises a second amplifier having an inverting input terminal connected to said reference electrode, a non-inverting input terminal of the second amplifier being connected to ground through said second source means for receiving the second reference voltage, the output of said second amplifier providing said continuous output signal Vo, and said first detecting means being connected between the inverting terminal of said second amplifier and the output terminal of said second amplifier.

8. The air fuel ratio measuring system according to claim 7, wherein said first detecting means comprises a resistor.

9. The air fuel ratio measuring system according to claim 8, wherein said second detecting means comprises a differential amplifier having its input terminals connected to opposite ends, respectively, of said resistor.

10. The air fuel ratio measuring system according to claim 7, wherein said second detecting means comprises a differential amplifier having input terminals respectively connected across said first detecting means.

* * * * *